United States Patent [19]
Raju et al.

[11] Patent Number: 5,348,973
[45] Date of Patent: Sep. 20, 1994

[54] RESOLUTION OF HYDROXYCHROMAN-2-CARBOXYLIC ACID ESTERS BY ENANTIOMERIC HYDROLYSIS

[75] Inventors: Muppala S. Raju, Bridgewater, N.J.; Namdol Huh, Ellicott City, Md.

[73] Assignee: Rhone-Poulenc Chimie, Courbevoie, France

[21] Appl. No.: 594,317

[22] Filed: Oct. 9, 1990

[51] Int. Cl.$^5$ .................... A01N 43/16; C07D 311/04
[52] U.S. Cl. .................................... 514/456; 514/457; 549/402
[58] Field of Search .................. 549/402; 514/456, 457

[56] References Cited

U.S. PATENT DOCUMENTS 4,801,605  1/1989  Hutchison ........................... 514/432

OTHER PUBLICATIONS

N. Cohen et al., "A Novel Total Synthesis of (2 R, 4′R, 8′R-α-Tocopherol (Vitamin E). Construction of Chiral Chromans from an Optically Active, Nonaromatic Precursor", *J.A.C.S. 101:22*, 6710 (Oct. 24, 1979).

J. B. Jones, "Enzymes in Organic Synthesis", *Tetrahedron 42:13*, 3351–3403 (October 1986).

A. Akiyama et al., "Enzymes in Organic Synthesis", *Chemtech*: 627–634 (October 1988).

C. H. Wong, "Enzymatic Catalysts in Organic Synthesis", *Science 244*: 1145–1152 (1989).

J. W. Scott et al., "6-Hydroxychroman-2-carboxylic acids: Novel Antioxidants", *J. Am. Oil Chem. Soc. 51*: 200–203 (1974).

*Primary Examiner*—C. Warren Ivy
*Assistant Examiner*—Raymond Covington
*Attorney, Agent, or Firm*—Paul J. Juettner

[57] ABSTRACT

Hydroxychroman-2-carboxylic acid esters can be resolved by enantiospecific hydrolysis by the use of liver enzymes, particularly solvent treated (acetone) enzymes. Liver enzymes from calf, cat, dog, eel, goat, lungfish, mouse, rat and seal have been found to be enantiospecific.

44 Claims, No Drawings

RESOLUTION OF HYDROXYCHROMAN-2-CARBOXYLIC ACID ESTERS BY ENANTIOMERIC HYDROLYSIS

FIELD OF THE INVENTION

This invention relates to the stereoselective enzymatic hydrolysis of esters of hydroxychroman-2-carboxylic acids to produce enantiomerically enriched acids using liver enzymes. The optical isomers can be used in the synthesis of vitamin E having structural equivalence to natural vitamin E, as antioxidants and as intermediates in the synthesis of enantiomerically pure drugs.

BACKGROUND OF INVENTION

Substituted 6-hydroxychroman-2-carboxylic acids have been used in the synthesis of vitamin E. Natural vitamin E has a 2 R configuration. However, present commercial synthesis of this compound has yielded an enantiomeric mixture at the 2-position. Some synthesis routes for vitamin E involve coupling a chroman moiety containing one asymmetric center with a $C_{14}$ or $C_{15}$ alkyl chain having two asymmetric carbon atoms. Enantiomerically pure chroman compounds required for the synthesis of natural vitamin E have been derived by classical resolution of their racemic mixtures or by steroselective synthesis from a chiral precursor [A Novel Synthesis of (2 R, 4' R, 8' R-alpha-Tacopherol (Vitamin E). Construction of Chiral Chromans from an Optically Active, Nonaromatic Precursor, N. Cohen et al. J.A.C.S. 101, 6710 (1979) and cited references]. 6-hydroxychroman- 2-carboxylic acid or 2-acetic acid have been resolved for optically active synthesis. Preparation of optically active acids and alcohols by stereospecific hydrolysis of esters or esterification of acids and alcohol by lipases and esterases have attracted wide attention and utilization [Enzymes in Synthesis, J. B. Jones, Tetrahedron 42, 3351–3403 (1986) and references cited therein; Enzymes in Organic Synthesis, A. Akiyama et al., Chemtech, 627–634 (1988); Enzymatic Catalysts in Organic Synthesis, C. H. Wong, Science, 244, 1145–1152 (1989)]. Enantiomerically pure chroman carboxylic acids, apart from their use in the synthesis of vitamin E in its natural form, have been used as antioxidants [6-Hydroxychroman-2-carboxylic acids: Novel Antioxidants, J. M. Scott et al., J. Am. Oil Chem. Soc. 51, 200–203 (1974)] and as drug intermediates [3,4-Dihydro-2H-1-benzopyran-2-carboxylic Acids and Related Compounds as Leukotriene Antagonists, N. Cohen et al., J. of Med Chem. 32, 1942–1860 (1989)].

In order to satisfy the need for optically active hydroxychroman-2-carboxylic acids, new methods of preparation are required.

SUMMARY OF THE INVENTION

Esters of hydroxychroman carboxylic acids can be resolved by enantiospecific hydrolysis using various liver enzymes, solvent treated liver enzymes and purified liver enzymes. The hydrolysis is preferably conducted in the presence of organic materials which are solvents for the esters and which assist in transport of the ester across the aqueous/organic interface to facilitate enzyme reaction in the aqueous phase. Stabilization of the purified and crude enzymes was found to be promoted by protease inhibitors. The enzyme can be immobilized on a solid support while retaining enzyme activity and without loss of enantiospecificity.

DETAILED DESCRIPTION OF THE INVENTION

The hydroxychroman carboxylic acid esters which can be enantiospecifically resolved by the process of the invention can be represented by Formula I:

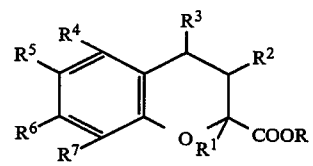

wherein R represents alkyl, alkaryl, haloalkyl and hydroxyalkyl; $R^1$ represents hydrogen, alkyl, arylalkyl, haloalkyl, hydroxyalkyl, oxoalkyl and $-R^8OR^9$ wherein $R^8$ & $R^9$ represent alkyl and aryl; $R^2$ and $R^3$ independently represent hydrogen, alkyl, arylalkyl, haloalkyl, hydroxyalkyl and oxoalkyl or when combined represent a double bond; $R^4$ through $R^7$ represent the same or independently different hydrogen, alkyl, arylalkyl, oxyalkyl, haloalkyl, hydroxyalkyl oxoalkyl and acyl wherein at least one is hydroxy. As used herein, the alkyl groups either alone or those which are substituted have from 1 to 8 and, preferably, 1 to 4 carbon atoms; halo is intended to include chlorine, bromine and iodine; aryl is intended to include up to two fused rings and acyl is intended to include fatty acids of up to 4 carbon atoms. Per convention, the hydrogens on the carbons to which are attached $R^2$ and $R^3$ are not shown.

Alkyl can be illustrated by methyl, ethyl, propyl and n-butyl; arylalkyl by benzyl; haloalkyl by 2-chloroethyl and chloromethyl; and hydroxyalkyl by 2-hydroxyethyl. Oxoalkyl can be the residue from aldehydes such as formaldehyde, acetaldehyde, propionaldehyde, and butyraldehyde or ketones such as dimethyl ketone, diethyl ketone, and ethyl phenyl ketone.

Acyl can be derived from lower fatty acids which include formic, acetic, propionic and butyric. An $-R^8OR^9$ group can be derived from ethers such as methyl ether, ethyl ether, ethyl methyl ether, ethyl propyl ether, ethyl phenyl ether and benzyl methyl ether.

R is preferably a lower alkyl of $C_1$ to $C_4$ carbon atoms, 2-hydroxyethyl or 2-chloroethyl; $R^1$ is preferably hydrogen, methyl, hydroxymethyl, benzyloxymethyl and formyl; $R^2$ and $R^3$ are preferably hydrogen or combined to form a double bond; $R^5$ is preferably hydroxy or acetyl and $R^4$, $R^6$ and $R^7$ are preferably independently hydrogen, ethyl, methyl, isopropyl, t-butyl and acetyl groups, with the qualification that when $R^5$ is acetyl, one of $R^4$, $R^6$ or $R^7$ is hydroxy.

The enzyme can be used in crude, solvent treated or purified form. The solvents which can be used to treat the enzyme include lower alcohols such as ethanol, lower alkyl ethers such as isopropyl ether and diethyl ether, hexane, isooctane and, preferably, acetone. The use of liver acetone powders has been found to be effective in practicing the invention.

The liver enzymes found to be effective in resolving hydroxychroman carboxylic acid esters can be obtained from the livers of calf, cat, dog, eel, goat, lungfish, mouse, rat and seal. Enzymes found ineffective include those from the livers of horse and rabbit. Any liver enzyme which is effective in resolving hydroxychroman carboxylic acids by hydrolysis of the esters can be used in the invention. Preferably, the liver enzymes are derived from goat, mouse and rat and, more preferably, goat.

Preferably, purified enzymes are utilized. The enzymes can be used as free enzymes or immobilized by conventional methods.

Suitable methods for immobilizing the enzyme for use herein are known in the art. See, for example, U.S. Pat. No. 4,436,813 which describes the immobilization of enzymes or cells containing the same using prepolymer materials such as polyazetidine prepolymers (e.e. Polycup), carboxymethyl cellulose, polymethylene isocyanate and polyurethane hydrogel prepolymers. Any of these materials may be used for present purposes in the manner described in U.S. Pat. No. 4,436,813. Also useful herein for immobilizing the enzyme are curable, polyfunctional aziridine prepolymers as described in U.S. Pat. No. 4,650,755 and Ser. No. 938,248, the contents of which are incorporated herein by reference. Additional immobilizing agents are illustrated in the examples given herein.

The enzymatic resolution can be carried out at any temperature range which is conducive to reaction and which does not inactivate the enzymes. High temperatures (i.e. >50° C.) are conducive to enzyme inactivation. Temperatures as low as 10° C. can be used though reaction rates are considerably lower. Effective temperatures vary somewhat depending on reactants and enzymes utilized. Advantageous results have been seen at temperatures ranging from about 25° C. to about 50° C., preferably from about 30° C. to about 40° C.

The pH utilized during the resolution reaction is that pH range conducive to efficient enzymatic reaction. While each enzyme has its own particular effective pH range, it has been found that pH's in general within the range of from about 5 to about 8.5 and preferably from about 6.5 to 7.5 are effective for the enzymes disclosed herein.

The reaction time used in the resolution is that time necessary to achieve the desired extent of reaction. Reaction times depend on the amount, type and purity of the enzyme, the substrate and can range from about one-half hour to several days.

The incubation reaction can be conducted in aqueous solution or in mixed aqueous solution/organic solvent systems. The organic solvents can be derived from such sources as hydrocarbons, aromatic hydrocarbons, ethers and aprotic polar organic solvents. The solvents which can be used include from zero to 99% by volume water-miscible organic solvent. Water-immiscible solvents can be used with water to form a two phase solvent system, which can comprise from about zero to about 50% by volume aqueous component and corresponding from about 100% to about 50% water-immiscible organic solvent.

The water-miscible organic solvents can be illustrated by alcohols such as $C_1$–$C_3$ alcohols and 1-methoxy-2-propanol, glycols such as propylene glycol, glycol ethers such as polyethylene glycol, polypropylene glycol, dimethyl ether of ethylene glycol, dimethyl ether of propylene glycol, dimethyl ether of diethylene glycol, dimethyl ether of tetraethylene glycol, and triols such as glycerol; cyclic oxides such as tetrahydrofuran and dioxane; ketones such as acetone and nitrogen containing compounds such as acetonitrile and dimethyl formamide and mixtures thereof.

The water-immiscible organic solvents can be illustrated by hydrocarbons such as hexane, heptane, isooctane, decane, hexadecane, kerosene, petroleum ether, toluene and xylenes; chlorinated hydrocarbon such as methylene chloride and chloroform; esters such as ethyl acetate; ethers such as propyl ether, isopropyl ether, butyl ether, isobutyl ether, diethyl ether, methyl ethyl ether and diphenyl ether; and alcohols such as 2-ethyl-1-hexanol, 2-octanol and mixtures thereof.

The resolved acids can be separated from the aqueous reaction solution by usual means including salting out and precipitation. The unresolved ester can be separated, racemized and recycled for further resolution.

Reducing agents in the aqueous resolution reaction mixture can be used to stabilize the generated acid against oxidation during the course of hydrolysis. Ascorbic acid, sodium metabisulfite and sodium sulfite have been found to be useful reducing agents to prevent the oxidation of the acids resulting from the hydrolysis. Generally, amounts ranging from about 1 mg to about 5 mg per ml of incubation solution have been found to be effective.

The following examples show the practice of this invention. Liver acetone powders for use in these examples were purchased from Sigma Chemical Company (St. Louis, Mo.), Amberlite DP-1 polystyrene/carboxylic acid ion exchange resin from Rohm-Haas (Philadelphia, Pa.); XAMA-2 polyaziridine and XAMA-7 [pentaenythrital-tris-(beta-N-aziridinyl) propionate] from Virginia Chemicals (Richmond, Va.); and 6-hydroxy 2,5,7,8-tetramethyl chroman-2-carboxylic acid from Aldrich Chemical Company (Milwaukee, Wis.).

Methyl and ethyl esters of 6-hydroxy-2,5,7,8-tetramethyl chroman-2-carboxylic acid were prepared by heating the acid solution in either 1% methanolic or ethanolic HCl solution and recrystallizing from toluene. The butyl ester was prepared by transesterification of the methyl ester with n-butanol in presence of p-toluenesulfonic acid and purification of the resulting n-butyl ester on a silica gel column.

All the compounds were characterized by using a HPLC $C_{18}$ Reverse Phase column (ISCO, Inc., Lincoln, Nebr.) and 200 MHz proton and 50 MHz carbon-13 NMR spectra.

EXAMPLE 1

Hydrolysis of Methyl-6-Hydroxy-2,5,7,8-Tetramethyl Chroman-2-Carboxylate with Liver Acetone Powder In a 20 ml scintillation vial, 25 mg of the above identified ester was dissolved (by sonification) in 1 ml of toluene. To this was added 9 ml of pH 7.6, 100 mM potassium phosphate buffer followed by the enzyme as identified and in the amounts given in Table I. The vials were stoppered and allowed to shake on a laboratory shaker (Junior Orbit Shaker, Lab Line Instruments Inc.) at 150 RPM for 16 hours. The vials were removed from the shaker, acidified with 6N HCl to pH 2 (indicated by pH paper) and extracted twice with 10 ml of ethyl acetate. From the aliquots of ethyl acetate extract, solvent was removed on a Savant Speed Vac and the resulting residue was dissolved in methanol for HPLC analysis on a $C_{18}$ Reverse Phase column and in a mobile phase mixture [hexane-isopropanol-glacial acetic acid (95:5:1)] for analysis on a Chiralcel-OG column (Daicel, Inc.). From the HPLC Reverse Phase and Chiralcel-OG column analysis chromatograms, the relative amounts of acid and ester were determined, and from Chiralcel-OG column analysis, the relative amounts of acid enantiomers were calculated. The following results were obtained:

TABLE I

Hydrolysis of Methyl Ester with Liver Acetone Powder

| ENZYME | AMOUNT | % EE | RATE* | % ACID |
|---|---|---|---|---|
| Liver Acetone Powder | | | | |
| 1. Mouse | 50 mg | 46 | 0.0310 | 36 |
| 2. Rat | 50 mg | 44 | 0.0327 | 38 |
| 3. Eel | 50 mg | 34 | 0.0353 | 41 |
| 4. Goat | 50 mg | 28 | 0.0542 | 63 |
| 5. Cat | 50 mg | 26 | 0.0585 | 68 |
| 6. Seal | 50 mg | 16 | 0.0387 | 45 |
| 7. Calf | 50 mg | 14 | 0.0387 | 45 |
| 8. Lungfish | 50 mg | 12 | 0.0224 | 26 |
| 9. Dog | 50 mg | 8 | 0.0267 | 31 |
| 10. Horse | 50 mg | 0 | 0.0757 | 88 |
| 11. Rabbit | 30 mg | 0 | 0.1218 | 85 |
| 12. Pig Liver enzyme | 1.52 mg | 4 | 0.7637 | 27 |

*Rate = uMoles/mg liver acetone powder/hr.

EXAMPLE 2

Hydrolysis of Ethyl-6-Hydroxy-2,5,7,8-Tetramethyl Chroman-2-Carboxylate with Goat Liver Acetone Powder A solution of the above identified ester dissolved in an organic solvent as listed in Table II below was admixed with 20 mg of goat liver acetone powder in 10 ml of aqueous phosphate buffer (ph 6.5–7), incubated and analyzed as in Example 1. The following results were obtained as reported in Table II.

TABLE II

| SOLVENT | % EE | RATE | % ACID |
|---|---|---|---|
| 1. Isopropyl ether - 1 ml | 80 | 0.118 | 42 |
| 2. Propyl ether - 1 ml | 70 | 0.118 | 42 |
| 3. Diphenyl ether - 1 ml | 62 | 0.096 | 34 |
| 4. Toluene - 1 ml | 60 | 0.087 | 31 |
| 5. Butyl ether - 1 ml | 48 | 0.107 | 38 |
| 6. Isobutyl ether - 1 ml | 24 | 0.093 | 33 |
| 7. Methyl ethyl ketone - 1 ml | 14 | 0.037 | 13 |
| 8. Heptane - 1 ml | 8 | 0.087 | 31 |
| 9. Aqueous buffer | 8 | 0.056 | 20 |
| 10. Acetone - 1 ml | 4 | 0.096 | 34 |
| 11. Dimethylforamide - 0.2 ml | 6 | 0.157 | 56 |
| 12. N-methyl-2-pyrrolidone - 0.2 ml | 6 | 0.152 | 54 |
| 13. Isooctane - 1 ml | 6 | 0.104 | 37 |
| 14. Dimethylsulfoxide - 0.2 ml | 4 | 0.124 | 44 |
| 15. 1,2-Dimethoxyethane - 1 ml | 4 | 0.129 | 46 |
| 16. Dichloromethane - 1 ml | 2 | 0.024 | 9 |
| 17. Tetrahydrofuran - 1 ml | — | 0.062 | 22 |

EXAMPLE 3

Purification of Enzyme from Goat Liver Acetone Powder

Goat liver acetone powder (3.5 gms) was solubilized in 140 ml of pH 6.0, 20 mM potassium phosphate buffer containing 2 mM EDTA and 1% Tween 80. After stirring for 1 hour at 4° C., the contents were centrifuged for 15 minutes at 12K on a Beckman J2-21 centrifuge. The separated supernatant was brought to 40% saturation with solid ammonium sulfate and allowed to stir for 1 hour at 4° C. The precipitate was removed by centrifugation as above, and the supernatant was further saturated to 60% with solid ammonium sulfate and stirred for 1 hour at 4° C. The precipitate was separated by centrifugation (same conditions as before), suspended in 140 ml of 20 mM pH 6.0, potassium phosphate buffer containing 2 mM EDTA and dialyzed against the same buffer (2.8 L) twice during 20 hours at 4° C. The dialyzate was loaded on a DEAE-Sepharose column (80 ml beads, 5×15 cm column) and equilibrated with the buffer (same as above, 20 times the column volume). The bound protein was eluted by stepwise salt gradients (0.1N and 0.2N NaCl solution, each with 1.5 times column volume) and the eluted fractions were assayed for stereospecific ester hydrolysis using the general procedure described in Example 1. The results are given in Table 3. All of the protein fractions were run on SDS-PAGE (10-15% GRADIENT) and IEF gel (pH 3–9) using the Pharmacia Phast System. The protein responsible for stereospecific hydrolysis of esters was determined to have a molecular weight around 60,000 and a pI around 4.6.

TABLE III

Hydrolysis of Ethyl 6-Hydroxy 2,5,7,8-Tetramethyl Chroman Carboxylate with Purification Fractions of Goat Liver Enzyme

| Enzyme Fraction | EE of Acid | % Acid |
|---|---|---|
| 1. Fraction II (0.2N NaCl elute) | 98 | 29 |
| 2. Fraction I (0.1N NaCl elute) | 66 | 46 |
| 3. Load | 66 | 5 |
| 4. Pass Through | — | 0 |

EXAMPLE 4

Immobilization of Enzyme

The enzyme solution (Fraction II, Example 3, 16 ml, 0.5 mgs of protein/ml) was mixed with 8.5 gms of Amberlite DP-1 and dried by lyophilization. The dry beads were added to 8 ml of 10 percent solution of XAMA-2 in toluene containing 400 ul of 1% stearic acid in toluene solution. The resulting mixture was stirred for 5 hours at room temperature and then excess toluene was evaporated under the hood. The beads (1 gm) were washed twice with 1 ml portions of the buffer (pH 7.6, 100 mm potassium phosphate) and the beads, buffer washings and 1 gm of beads without washing were tested for hydrolysis of ethyl ester of 6-hydroxy-2,5,7,8-tetramethyl chroman carboxylate. The buffer washings did not have any enzyme activity. The unwashed beads had 80% of the activity of the same amount of enzyme in solution and the washed beads around 70% of the activity, both with an EE of 98%.

EXAMPLE 5

Hydrolysis of Ethyl 6-Hydroxy-2,5,7,8-Tetramethyl Chroman-2-Carboxylate with Goat Liver Acetone Powder in Presence of Acid Stabilizing Reducing Agents Using the general procedure of Example 1, the above identified ethyl ester was hydrolyzed in buffer containing the reducing agents shown in Table IV. Work up and analysis of the product on a Chiralcel-OG column gave twin peaks at 9.7 to 10.3 minutes corresponding to the acid decomposition products and at 15.8 and 17.8 minutes for the two enantiomeric acids using 95:5:1 (volume ratio) mixture of hexane-isopropyl alcohol and glacial acetic acid as a mobile phase. Table IV shows the ratio of peaks (two) eluting at 9.7 to 10.3 minutes to two acid enantiomer peaks eluting at 15.8 and 17.8 minutes.

TABLE IV

Stabilization of 6-Hydroxy-2,5,7,8-Tetramethyl Chroman Carboxylic Acid in Presence of Reducing Agents

| Sample No. | Adjuvant | % of 9.7 to 10.3 min peaks | % of 15.8 to 17.8 min peaks |
|---|---|---|---|
| 1. | None | 31 | 69 |
| 2. | 20 ul of Mercaptoethanol | 34 | 66 |
| 3. | 10 mgs of Ascorbic Acid | 20 | 80 |
| 4. | 10 mgs of Sodium Metabisulfite | 11 | 89 |
| 5. | 25 mgs of Sodium Sulfite | 12 | 88 |

EXAMPLE 6

Hydrolysis of Ethyl 6-Hydroxy-2,5,7,8-Tetramethyl chroman Carboxylate with Goat Liver Acetone Powder Buffer Extract To a mixture of 500 mgs of the above noted ethyl ester in 20 ml of isopropyl ether and 200 ml of 100 mM potassium phosphate buffer (pH 7.6) containing 400 mgs of sodium sulfite was added 20 ml of goat liver acetone powder buffer extract as in Example 3 and the mixture was left shaking on a mini lab shaker in an IL Erien Meyer Flask for 20 hours. The mixture contents were then extracted with two 200 ml portions of dichloromethane and the organic layers were separated by centrifugation. The aqueous layer was acidified with 6N HCl to a pH of about 2.0 and extracted with three 180 ml portions of dichloromethane. Both dichloromethane extracts were evaporated separately, the first containing, predominantely, the ester and the second extract, predominately, acid. Both the ester and acid were purified on a silica gel column using a hexane/ethyl acetate mixture as eluting solvent to yield 200 mgs of ethyl ester [alpha 20 d]=−41.45 (c, 0.11 in ethanol), and 220 mgs of the carboxylic acid [alpha 20 d]+46.2 (c, 0.1 in ethanol). Both proton and carbon-13 NMR spectra corresponded to the expected compounds.

What is claimed is:

1. A process for resolving by enantiospecific hydrolysis carboxylic acid esters which are the methyl or ethyl esters of 6-hydroxy-2,5,7,8-tetramethyl-chroman-2-carboxylic acid comprising the step of hydrolyzing said esters with an animal liver enzyme derived from an animal selected from the group consisting of calf, cat, dog, eel, goat, lungfish, mouse, rat and seal;

wherein percent acid produced upon hydrolysis is at least about 26% and percent enantiomeric excess of said resolved acid is at least about 8%.

2. The method as recited in claim 1 wherein the hydroxychroman carboxylic acid esters are the methyl and ethyl esters of 6-hydroxy-2,5,7,8-tetramethyl chroman-2-carboxylic acid.

3. The method recited in claim 1 wherein the liver enzyme is in crude form, solvent treated liver enzyme or a purified liver enzyme.

4. The method as recited in claim 3 wherein the liver enzyme is a solvent treated liver enzyme and the solvent is acetone.

5. The method as recited in claim 1 wherein the liver enzyme is immobilized on a solid support.

6. The method as recited in claim 5 wherein the enzyme is immobilized by absorbing the enzyme on an ion exchange resin followed by contacting the so absorbed enzyme with a polyaziridine prepolymer in the presence of a fatty acid.

7. The method as recited in claim 1 wherein the hydrolysis is conducted in an aqueous phase in the presence of an organic solvent for the ester.

8. The method as recited in claim 7 wherein the solvent is a hydrocarbon solvent, an aromatic hydrocarbon solvent or an aprotic polar organic solvent.

9. The method as recited in claim 7 wherein the solvent is an aliphatic or aromatic ether.

10. The method as recited in claim 9 wherein the ether is selected from the group consisting of propyl ether, isopropyl ether, butyl ether, isobutyl ether and diphenyl ether.

11. The method as recited in claim 7 wherein the organic solvent is toluene or xylenes.

12. The process of claim 1 additionally comprising stabilizing the enzyme with a protease inhibitor.

13. The method of claim 1 additionally comprising immobilizing the enzyme with a prepolymer of at least one of polyazetidine, carboxymethyl cellulose, polymethylene isocyanate, polyurethane hydrogel and polyfunctional aziridine.

14. The method of claim 1 wherein said hydrolyzing is carried out at a temperature of below about 50° C.

15. The method of claim 1 wherein said hydrolyzing is carried out at a temperature as low as about 10° C.

16. The method of claim 1 wherein said hydrolyzing is carried out at a temperature of about 25° C. to about 50° C.

17. The method of claim 1 wherein said hydrolyzing is carried out at a temperature of about 30° C. to about 40° C.

18. The method of claim 1 wherein said hydrolyzing is carried out at a pH of from about 5 to about 8.5.

19. The method of claim 18 wherein said pH is from about 6.5 to about 7.5.

20. The method of claim 1 wherein said hydrolyzing ranges from about one half hour to about several days.

21. The method of claim 1 wherein said hydrolyzing is carried out in an aqueous solution or in a mixed aqueous solution-organic solvent system.

22. The method of claim 21 additionally comprising separating the resolved acid from solution by salting out or precipitation.

23. The method of claim 1 additionally comprising stabilizing the resolved acid against oxidation during the course of hydrolysis by adding a reducing agent.

24. The method of claim 23 wherein said reducing agent is selected from at least one of ascorbic acid, sodium metabisulfite and sodium sulfite.

25. The method of claim 23 additionally comprising adding said reducing agent in an amount ranging from about 1 mg/ml to 5 mg/ml.

26. The method of claim 22 wherein said mixed aqueous solution-organic solvent system comprises from about zero to about 99% by volume water-miscible organic solvent.

27. The method of claim 26 wherein said water-miscible solvent is selected from at least one of alcohols, glycols, glycol ethers, triols, cyclic oxides, ketones and nitrogen-containing compounds.

28. The method of claim 27 wherein said water-miscible solvent is selected from at least one of $C_1$–$C_3$ alcohols, 1-methoxy-2-propanol, propylene glycol, polyethylene glycol, polypropylene glycol, dimethyl ether of ethylene glycol, dimethyl ether of propylene glycol, dimethyl ether of diethylene glycol, dimethyl ether of tetraethylene glycol, glycerol, tetrahydrofuran, dioxane, acetone, acetonitrile and dimethyl formamide.

29. The method of claim 22 wherein said mixed aqueous solution—organic solvent system comprises from about zero to about 50% by volume aqueous component and from about 100% to about 50% water immiscible organic solvent component to form a two phase system.

30. The method of claim 29 wherein said water-immiscible solvent is selected from at least one of hydrocarbons, chlorinated hydrocarbons, esters, ethers and alcohols.

31. The method of claim 30 wherein said water-immiscible solvent is selected from at least one of hexane, heptone, isooctane, decane, hexadecane, kerosene, petroleum ether, toluene, xylenes, methylene chloride, chloroform, ethyl acetate, propyl ether, isopropyl ether, butyl ether, isobutyl ether, diphenyl ether, 2-ethyl-1-hexanol and 2-octanol.

32. The method of claim 1 wherein said enantiomeric excess of said resolved acid is at least about 28%.

33. The process of claim 1 wherein
said liver enzyme is derived from an animal selected from the group consisting of goat, mouse and rat,
the percent acid produced upon hydrolysis is at least about 36%, and
the percent enantiomeric excess of said resolved acid is at least about 28%.

34. The process of claim 1 wherein said esters are hydrolyzed with acetone powder containing said animal liver enzyme.

35. The process of claim 1 wherein methyl ester of 6-hydroxy-2,5,7,8-tetramethylchroman-2-carboxylic acid is hydrolyzed.

36. The process of claim 1 wherein ethyl ester of 6-hydroxy-2,5,7,8-tetramethylchroman-2-carboxylic acid is hydrolyzed.

37. The process of claim 36 wherein the animal liver enzyme is derived from goat.

38. The process of claim 37 wherein
the enzyme is treated with a solvent selected from the group consisting of isopropyl ether, propyl ether, diphenyl ether, toluene, butyl ether and isobutyl ether,
the percent acid produced upon hydrolysis is at least about 31%, and
the percent enantiomeric excess of said resolved acid is at least about 24%.

39. The process of claim 37 wherein said enzyme is initially purified by loading upon a DEAE-Sepharose column, equilibrating with buffer, and stepwise eluting with salt gradients, and
the resulting enantiomeric excess of resolved acid is at least about 66%.

40. The process of claim 37 wherein
said enzyme is initially immobilized by adsorbing on a resin followed by contacting with XAMA-2 solution in the presence of a fatty acid,
and the enantiomeric excess of resolved acid is at least about 98%.

41. The process of claim 37 wherein hydrolysis is conducted in the presence of a reducing agent selected from the group consisting of mercaptoethanol, ascorbic acid, sodium metabisulfite and sodium sulfite.

42. The method of claim 1 comprising the additional step of
recovering at least one resolved enantiomer of said acid.

43. The method of claim 1 additionally comprising
initially esterifying a racemic mixture of 6-hydroxy-2,5,7,8-tetramethylchroman-2-carboxylic acid.

44. The method of claim 1 wherein said esters are $C_1$ to $C_4$ alkyl esters of 6-hydroxy-2,5,7,8-tetramethylchroman-2-carboxylic acid.

* * * * *